(12) United States Patent
Jameson et al.

(10) Patent No.: US 8,226,993 B2
(45) Date of Patent: Jul. 24, 2012

(54) NON-TOXIC ANTI MICROBIAL COMPOSITION

(76) Inventors: Simon Jameson, Santa Barbara, CA (US); Bruce Jameson, Manhattan Beach, CA (US)

( * ) Notice: Subject to any disclaimer, the term of this patent is extended or adjusted under 35 U.S.C. 154(b) by 0 days.

(21) Appl. No.: 12/911,731

(22) Filed: Oct. 26, 2010

(65) Prior Publication Data

US 2011/0038964 A1 Feb. 17, 2011

Related U.S. Application Data

(62) Division of application No. 12/124,762, filed on May 21, 2008, now abandoned.

(60) Provisional application No. 60/995,737, filed on Sep. 27, 2007.

(51) Int. Cl.
*A01N 65/00* (2009.01)
(52) U.S. Cl. ........................................ 424/725
(58) Field of Classification Search .................. None
See application file for complete search history.

(56) References Cited

U.S. PATENT DOCUMENTS

2003/0096722 A1* 5/2003 Caselli et al. ................. 510/382
* cited by examiner

*Primary Examiner* — Michael Meller
(74) *Attorney, Agent, or Firm* — Ash Tankha; Lipton, Weinberger & Husick

(57) ABSTRACT

Disclosed herein are non-toxic antimicrobial compositions for cleaning, reducing the bioburden and substantially killing gram negative and positive bacteria on hard surfaces. The antimicrobial compositions comprise about 0.01% to about 4.0% by weight of one or more oils selected from the group comprising rosemary oil, tea tree oil, spearmint oil, peppermint oil, clove oil, lemongrass oil, cedar oil, and cinnamon oil and about 0.1% to about 4.0% by weight of one or more acids selected from the group comprising carboxylic acids, ascorbic acid, glutamic acid, fumaric acid, oxalic acid and malonic acid. In an embodiment of the invention, an alkali base such as sodium hydroxide or potassium hydroxide is added to the above antimicrobial solution to increase the pH of the antimicrobial solution to a range of about 2.0 to about 4.0 to effect a rapid reduction of the bioburden on the hard surfaces within 5 minutes.

3 Claims, 2 Drawing Sheets

| EXAMPLE NO. | ACETIC ACID | ROSEMARY OIL | SPEARMINT OIL | SODIUM HYDROXIDE | pH |
|---|---|---|---|---|---|
| 4 | 4.0% | 0.1% | 0.1% | 0.25% | 3.5 |
| 5 | 3.5% | 0.25% | 0.2% | 0.1% | 3.2 |
| 6 | 2.5% | 0.025% | 0.15% | 0.5% | 3.8 |
| 7 | 3.0% | 0.8% | 0.2% | 0.1% | 3.5 |

FIG. 1

| EXAMPLE NO. | COMPOSITION OF THE NON TOXIC ANTIMICROBIAL SOLUTION | MICROBIAL RECOVERY, COLONY FORMING UNITS (MICROORGANISMS/MILLILITER) | | | |
|---|---|---|---|---|---|
| | | STAPHYLOCOCCUS AUREUS | | PSEUDOMONAS AERUGINOSA | |
| | | 5 MINUTES CONTACT TIME | 10 MINUTES CONTACT TIME | 5 MINUTES CONTACT TIME | 10 MINUTES CONTACT TIME |
| 8 | 2% ACETIC ACID AND 0.1% ROSEMARY OIL, AT PH 2.8 | 15800 | 6300 | LESS THAN 10 | LESS THAN 10 |
| 9 | 4% ACETIC ACID AND 0.1% ROSEMARY OIL, AT PH 2.8 | 3300 | LESS THAN 10 | LESS THAN 10 | LESS THAN 10 |
| 10 | 2% ACETIC ACID, 0.1% ROSEMARY OIL, AND 0.25% SODIUM HYDROXIDE AT PH 3.5 | 2200 | 45 | LESS THAN 10 | LESS THAN 10 |
| 11 | 4% ACETIC ACID, 0.1% ROSEMARY OIL, AND 0.25% SODIUM HYDROXIDE AT PH 3.5 | 268 | LESS THAN 10 | LESS THAN 10 | LESS THAN 10 |

FIG. 2

| EXAMPLE NO. | COMPOSITION OF THE NON TOXIC ANTIMICROBIAL SOLUTION | MICROBIAL RECOVERY, COLONY FORMING UNITS (MICROORGANISMS/MILLILITER) AFTER 10 MINUTES OF CONTACT WITH THE PRODUCT | | | |
|---|---|---|---|---|---|
| | | STAPHYLOCOCCUS AUREUS | PSEUDOMONAS AERUGINOSA | ESCHERICHIA COLI | SALMONELLA |
| 12 | 4% ACETIC ACID, 0.25% SODIUM HYDROXIDE, 1% ROSEMARY OIL, AND 1% SPEARMINT OIL | LESS THAN 10 | LESS THAN 10 | LESS THAN 10 | LESS THAN 10 |

FIG. 3

NON-TOXIC ANTI MICROBIAL COMPOSITION

CROSS REFERENCE TO RELATED APPLICATIONS

This application is a divisional of patent application Ser. No. 12/124,762 titled "Non toxic antimicrobial Composition", filed on May 21, 2008, now abandoned in the United States Patent and Trademark Office, which claims the benefit of the provisional patent application U.S. 60/995,737 titled "Non-toxic Anti Microbial Composition", filed on Sep. 27, 2007 in the United States Patent and Trademark Office.

BACKGROUND

This invention, in general, relates to antimicrobial compositions for sanitizing surfaces. More particularly, this invention relates to a non-toxic antimicrobial aqueous composition that can be used to clean, reduce the bioburden and substantially kill gram positive and negative bacteria on hard surfaces.

Typically, surfaces in many residential, office, and other facilities may be difficult for the custodial staff to adequately clean and sanitize. The composition and texture of such surfaces generally harbor bioburden and organic mater that may not be effectively removed from the surfaces using standard cleaning procedures and disinfectants. As a result of using ineffective antimicrobial agents, the surfaces may accumulate microbial flora and organic matter that may become a source of non-hygienic or unsanitary conditions.

Therefore, there is a need for a non-toxic antimicrobial solution to clean, reduce the bioburden and substantially kill gram positive and negative bacteria on hard surfaces including the microbial flora, molds, bacteria, yeast, and viruses and organic matter present on hard surfaces.

Furthermore, many disinfectants contain surfactants that cause skin allergies. Therefore, there is also a need for the non-toxic antimicrobial solution to be hypoallergenic.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

FIG. 1 summarizes the data of examples 1-4 for preparing the non-toxic antimicrobial solution for cleaning, sanitizing, and reducing the bioburden on hard surfaces.

FIG. 2 exemplarily illustrates the effect of non-toxic antimicrobial compositions comprising acetic acid, rosemary oil, and sodium hydroxide on bioburden reduction.

FIG. 3 exemplarily illustrates the effect of the non-toxic antimicrobial composition comprising acetic acid, rosemary oil, spearmint oil, and sodium hydroxide on bioburden reduction.

DETAILED DESCRIPTION OF THE INVENTION

Disclosed herein are antimicrobial compositions used for preparing a non-toxic antimicrobial solution to clean, reduce the bioburden and substantially kill gram positive and negative bacteria on hard surfaces. As used herein, microbial flora, molds, bacteria, yeast, viruses, organic matter, etc., present on hard surfaces are collectively referred to as "bioburden". The hard surfaces comprise table surfaces, equipment surfaces, cutting boards, food processing equipment, food storage equipment, plastic containers, metal containers, conveyor belts, etc. The non-toxic antimicrobial solution does not contain any volatile component or solvents such as alcohol. The antimicrobial compositions comprise hypo allergens. Therefore, the antimicrobial compositions are safe, emission compliant, non-toxic, and hypoallergenic.

The antimicrobial composition for preparing the non-toxic antimicrobial solution comprises about 0.01% to about 4.0% by weight of one or more essential oils selected from the group comprising rosemary oil, tea tree oil, spearmint oil, peppermint oil, clove oil, lemongrass oil, cedar oil, and cinnamon oil, and about 0.1% to about 4.0% by weight of one or more acids selected from the group comprising carboxylic acids, ascorbic acid, glutamic acid, fumaric acid, oxalic acid, and malonic acid, where the % weights are based on the total weight of the antimicrobial solution. The antimicrobial solution substantially kills the gram negative and gram positive bacteria on hard surfaces in about 10 minutes.

Herein, the term "substantially kills" means reduction of bacteria by the antimicrobial solution to less than 10 microorganisms per gram or per milliliter of the antimicrobial solution when the antimicrobial solution is incubated with the bacteria in accordance with the challenge protocol described below.

The carboxylic acids comprise acetic acid, citric acid, formic acid, propionic acid, lactic acid, malic acid, glycolic acid, butyric acid, etc. The oils comprising rosemary oil, spearmint oil, peppermint oil, clove oil, lemongrass oil, cedar oil, cinnamon oil, etc. are herein referred to as essential oils.

In an embodiment of the invention, the antimicrobial composition comprises about 0.01% to about 4.0% by weight of one or more essential oils, about 1.0% to about 4.0% by weight of a carboxylic acid, and about 0.1% to about 0.5% by weight of an alkali base sufficient to increase pH of the antimicrobial solution to a range of about 2.0 to about 4.0, wherein the % weights are based on the total weight of the antimicrobial solution. The non-toxic antimicrobial solution of this embodiment substantially kills the gram negative bacteria and the gram positive bacteria on hard surfaces in about 5 minutes. It was found that addition of the alkali base to the antimicrobial solution increases the kill rate of the bioburden and obviates the acidic smell and feel of the acids in the antimicrobial composition.

Alkali bases comprise sodium hydroxide, potassium hydroxide, etc.

The following procedure is followed to test for the anti microbial effectiveness of the antimicrobial solution. Herein this procedure will be referred to as the challenge protocol. The materials used for verifying the antimicrobial effectiveness of the non-toxic antimicrobial solution comprise an autoclave, sterile petri dishes, sterile pipettes of volume 1 milliliter and 10 milliliters, sterile tongue depressors, deionized water (DI), sterile saline, sterile saline with 0.05% polysorbate 20, sterile screw cap tubes, sterile screw cap culture tubes, pH paper, tryptic soy agar (TSA), sabouraud dextrose agar (SDA), microbial content test agar (MCTA), a weighing scale, inoculating loops, an incubator at 30° to 35° C., and a refrigerator capable of maintaining 2° C. to 8° C. temperature. The microorganisms used for challenging the antimicrobial effectiveness of the antimicrobial solution comprise *escherichia coli, staphylococcus aureus, enterobacter cloacae, klebsiella pneumoniae, pseudomonas aerugi-* nosa, *burkholderia cepacia, pseudomonas fluorescens, pseudomonas putida, candida albicans,* and *aspergillus niger.*

The following challenge protocol is followed to test the antimicrobial efficacy of the antimicrobial compositions disclosed herein.

Preparation of bacterial inocula: Re-hydrated stock microorganisms are streaked onto the surface of previously prepared TSA plates 24 hours prior to inoculating bacterial suspensions into the products. The TSA plates are incubated at a temperature of 30°-35° C. for 18 to 24 hours. A sterile inoculating loop is used to pick 3-5 good size colonies from the surface of the agar plates. The sterile inoculating loop is inserted into a 5 milliliter sterile saline tube and the sterile inoculating loop is rotated against the wall vigorously to release microorganisms. The suspension tubes are vortexed to evenly disperse the microorganisms in the saline. In order to use the suspension immediately, a laboratory reference, established previously, is used to adjust the turbidity of the suspension, so that 0.1 milliliter of the suspension delivers $10^6$ bacteria per gram or per milliliter of the product. The original suspension is estimated to have $2 \times 10^8$ bacteria per milliliter. When 0.1 milliliter of the bacterial suspension is inoculated into 20 gram or per milliliter of the product, the suspension will deliver $10^6$ bacteria per gram or per milliliter of the product.

To count the actual number of microorganisms in the suspension, serial dilutions of each suspension up to $10^9$ dilutions with 4.5 milliliter sterile saline tubes are prepared. Plate count method is used to obtain the number of colony forming units (CFU). 1 milliliter of $10^7$, $10^8$, and $10^9$ dilutions are placed in each of two sterile petri dishes and 15 to 20 milliliters of TSA is poured on them. The dilutions are mixed by rotating three times in clockwise and three times in counter-clockwise direction. The agar is allowed to solidify. The plates are incubated at 30° to 35° C. for 24 hours and the number of CFU is counted on the agar plates to determine the microbial count in the original suspension tubes. In-house isolates are also cultured and serially diluted to obtain working inocula for PET.

Preparation of *candida albicans*: *Candida albicans* stock is re-hydrated and streaked on SDA for growth 2 days prior to preparing the inoculum. The procedure described for the preparation of bacterial inocula is followed for harvesting and inoculation of *candida albicans* into products.

Preparation of *aspergillus niger*: *Aspergillus niger* stock is re-hydrated and streaked on the surface of a previously prepared SDA plate and incubated at 20°-25° C. for a minimum of 7 days or until good sporulation is obtained. Sterile saline with 0.05% polysorbate 80 is used to collect the spores. 15 to 20 milliliters of saline is poured over the growth of *aspergillus niger* and agitated to dislodge the spores.

The spore suspension is filtered through sterile gauze to filter out conidia and hyphae and then the suspension is transferred into a sterile tube. The spore suspension is filtered through sterile gauze for filtering out conidia and hyphae and the suspension is then transferred into a sterile tube. Up to $10^4$ serial dilution of the suspension is made and the spores in the $10^3$ and $10^4$ tubes are counted using a hemacytometer. The original suspension is adjusted to have $2 \times 10^7$ spores per milliliter. When 0.1 milliliter of the suspension is inoculated into 20 grams or milliliters of the product, the suspension will deliver $10^5$ spores per gram or per milliliter of the product. Plate the dilutions with SDA to determine the number of viable spores in the original suspension.

Procedure: 20 milliliter portions of the test material are aseptically transferred into sterile containers. Each of the tubes is inoculated with the corresponding microorganisms. 0.05 milliliter of the microbial suspensions is transferred from serial dilution tubes to inoculate $1 \times 10^6$ bacteria and $1 \times 10^5$ yeast or mold per milliliter of test sample. The sample is mixed thoroughly to obtain an even distribution of the microorganisms in the sample with the same pipette that is used to transfer microbial suspension. The tubes are examined immediately after inoculation at times periods specified by the client. Plate count method (TPC) is used to determine the number of viable microorganisms present at each of these time intervals. Growth promotion (GP) and sterility testing is performed on the media used for pour plating. Since the media used for pour plating is prepared on the day of use, GP and sterility testing will serve as positive and negative controls. GP and sterility testing are performed on the media used for pour plating. Since the media used for pour plating is prepared on the day of use, GP and sterility testing will serve as Positive and Negative controls. If microbial growth is detected on the TPC plates, using the theoretical concentration of microorganisms present at the start of the test, the percentage change in the concentration of each microorganism is measured during the test. If no growth is detected on the plates, the results are reported as less than 10 microorganisms per gram or per milliliter of the product.

Verification of preservative neutralization: Preservative neutralization is verified in order to make sure preservatives are properly neutralized and absence of growth on the recovery plate is not due to preservative carry over from diluents to the recovery medium during plate count procedure. Test organisms are streaked on the surface of the recovery medium after the completion of the first test interval. Serial dilution tubes are used to streak 10 to 100 test organisms on the surface of the recovery plate 0.1 milliliter of the microbial suspension is transferred, thereby yielding 10 to 100 organisms on the plate. Positive controls are set up by streaking the same number of microorganisms on fresh MCTA plates. The recovery plates and positive controls are re-incubated and the challenge organisms on the surface are observed for growth. If growth is not apparent on the recovery plates after incubation, neutralization of the preservative system is inadequate and an appropriate neutralizer must be found. When neutralizers are not available or effective, physical dilution or membrane filtration may be performed to recover surviving microorganisms from the sample.

The examples below illustrate the composition, method of preparation and efficacy of the non-toxic antimicrobial solution. All components in the antimicrobial compositions listed below are by weight percent. For example, the acetic acid in example 1 is 2% by weight. The antimicrobial solution is prepared by weighing the components into a container and mixing them. Where an alkali base is added to the antimicrobial solution, the alkali base may be weighed out and then added to the antimicrobial solution, or added directly to the antimicrobial solution till the antimicrobial solution reaches the desired pH level.

EXAMPLE 1

The antimicrobial solution comprises 2% acetic acid, 0.1% rosemary oil: and 97.9% water, the % weights based on the total weight of the antimicrobial solution. The antimicrobial solution of this example substantially kills the gram negative and gram positive bacteria on hard surfaces in about 10 minutes.

EXAMPLE 2

The antimicrobial solution comprises 2% acetic acid, 0.3% rosemary oil: and 97.7% water, the % weights based on the total weight of the antimicrobial solution. The antimicrobial solution of this example substantially kills the gram negative bioburden and the gram positive bioburden on hard surfaces in about 10 minutes.

EXAMPLE 3

The antimicrobial solution comprises 1% acetic acid, 1% ascorbic acid, 0.4% spearmint oil and 97.6% by weight water; the % weights based on the total weight of the antimicrobial solution. The antimicrobial solution of example 3 substantially kills the gram negative bioburden and the gram positive bioburden on hard surfaces in about 10 minutes.

An alkali base may be added to each of the compositions recited in examples 1-3 sufficient to increase the pH of the antimicrobial solution to a range of about 2.0 to about 4.0.

EXAMPLE 4

The antimicrobial solution comprises 4% acetic acid, 0.1% of rosemary oil, 0.1% spearmint oil, and about 0.25% of sodium hydroxide sufficient to increase the pH of the solution to 3.5, and sufficent water to adjust the total weight % of the composition to 100% the % weights based on the total weight of the antimicrobial solution. The antimicrobial solution of this example reduces the bioburden and substantially kills the gram negative bioburden and the gram positive bioburden on hard surfaces in about 5 minutes.

EXAMPLE 5

The antimicrobial solution comprises 3.5% of acetic acid, 0.25% of rosemary oil, 0.2% spearmint oil, about 0.1% of sodium hydroxide sufficient to increase the pH to 3, and sufficent water to adjust the total weight % of the composition to 100%, the % weights based on the total weight of the antimicrobial solution. The antimicrobial solution of this example reduces the bioburden and substantially kills the gram negative bioburden and the gram positive bioburden on hard surfaces in about 5 minutes.

EXAMPLE 6

The antimicrobial solution comprises 2.5% of acetic acid, 0.025% of rosemary oil, 0.15% spearmint oil, and about 0.5% of sodium hydroxide sufficient to increase the pH of the composition to 3.8, and sufficent water to adjust the total weight % of the composition to 100%, the % weights based on the total weight of the antimicrobial solution. The antimicrobial solution reduces the bioburden and substantially kills all the gram negative bioburden and the gram positive bioburden on hard surfaces in about 5 minutes.

EXAMPLE 7

The antimicrobial solution comprises 3.0% of acetic acid, 0.8% of rosemary oil, 0.2% spearmint oil, about 0.1% of sodium hydroxide sufficient to increase the pH of the composition to 3.5, and sufficent water to adjust the total weight % of the composition to 100%, the % weights based on the total weight of the antimicrobial solution. The antimicrobial solution substantially kills all the gram negative bioburden and the gram positive bioburden on hard surfaces in about 3 minutes.

Tea tree oil and spearmint oil may also be added to the compositions of example 4-7 as an antibacterial fragrance.

FIG. 2 exemplarily illustrates the effect of the non-toxic antimicrobial compositions comprising acetic acid, rosemary oil, sodium hydroxide and sufficent water to adjust the total weight % of the composition to 100%, on bioburden reduction and gram positive and negative bacteria. The effect of the non-toxic antimicrobial solution on *staphylococcus aureus* and *pseudomonas aeruginosa* is tabulated. *Staphylococcus aureus* is a gram positive bacterium; *pseudomonas aeruginosa* is a gram negative bacterium. *Staphylococcus aureus* is a common cause of staph infections. *Staphylococcus aureus* is a spherical bacterium, frequently living on the skin or in the nose of a person. *Staphylococcus aureus* may can cause a range of illnesses from 15 minor skin infections, such as pimples, impetigo, boils, cellulitis and abscesses, to life threatening diseases, including pneumonia, meningitis, endocarditis, toxic shock syndrome, and septicemia.

*Pseudomonas aeruginosa* is an opportunistic pathogen causing hospital acquired infections, particularly in predisposed patients with metabolic, hematologic, and malignant diseases. *Pseudomonas aeruginosa* produces toxic factors such as lipase, esterase, lecithinase, elastase, and endotoxin.

The antimicrobial solution is challenged with an initial inoculum of the microorganisms of 1,000,000 microorganisms per milliliter. The expression "less than 10" as shown in FIG. 2 denotes no microbial recovery. In the examples below, the colony forming units of the *staphylococcus aureus, escherichia coli, salmonella*, and *pseudomonas aeruginosa* are measured in microorganisms per milliliter.

EXAMPLE 8

The antimicrobial solution comprises 2% acetic acid, 0.1% rosemary oil, and sufficent water to adjust the total weight % of the composition to 100%, the % weights based on the total weight of the antimicrobial solution. The antimicrobial solution has a pH of 2.8. The antimicrobial solution is incubated with *Staphylococcus aureus* in accordance with the challenge protocol. The colony forming units of the *staphylococcus aureus* after 5 minutes is 15,800 microorganisms per milliliter. The colony forming units of the *staphylococcus aureus* after 10 minutes is 6,300 microorganisms per milliliter. The antimicrobial solution is then incubated with *Pseudomonas aeruginosa* in accordance with the challenge protocol. The colony forming units of the *pseudomonas aeruginosa* after 5 minutes is less than 10 microorganisms per milliliter indicating substantial kill of the microorganism. The colony forming units of the *pseudomonas aeruginosa* after 10 minutes remains less than 10 microorganisms per 10 milliliter.

EXAMPLE 9

The antimicrobial solution of example 9 comprises 4% acetic acid, and 0.1% rosemary oil, and sufficent water to adjust the total weight % of the composition to 100%, the % weights based on the total weight of the antimicrobial solution. The non-toxic antimicrobial solution has a pH of 2.8. The antimicrobial solution is incubated 15 with *staphylococcus aureus* in accordance with the challenge protocol. The colony forming units of the *staphylococcus aureus* after 5 minutes is 3,300 microorganisms per milliliter. The colony forming units of the *staphylococcus aureus* after 10 minutes is less than 10 microorganisms per milliliter. The antimicrobial solution is then incubated with *Pseudomonas aeruginosa* in accordance with the challenge protocol. The colony forming 20 units of the *pseudomonas aeruginosa* after 5 minutes is less than 10 microorganisms per milliliter indicating substantial kill of the microorganism. The colony forming units of the

*pseudomonas aeruginosa* after 10 minutes remains less than 10 microorganisms per milliliter.

EXAMPLE 10

The non-toxic antimicrobial solution comprises the following constituents: 2% acetic acid, 0.1% rosemary oil, about 0.25% sodium hydroxide sufficient to increase the pH of the antimicrobial solution to 3.5, and suffcent water to adjust the total weight % of the composition to 100%, the % weights based on the total weight of the antimicrobial solution. The antimicrobial solution is incubated with *staphylococcus aureus* in accordance with the challenge protocol. The colony forming 30 units of the *staphylococcus aureus* after 5 minutes is 2,200 microorganisms per milliliter. The colony forming units of the *staphylococcus aureus* after 10 minutes is 45 microorganisms per milliliter. The antimicrobial solution is then incubated with *pseudomonas aeruginosa*. The colony forming units of the *pseudomonas aeruginosa* after 5 minutes is less than 10 microorganisms per milliliter indicating substantial kill of the microorganism. The colony forming units of the *pseudomonas aeruginosa* after 10 minutes remains less than 10 microorganisms 5 per milliliter.

EXAMPLE 11

The non-toxic antimicrobial solution comprises 4% acetic acid, 0.1% rosemary oil, about 0.25% sodium hydroxide, sufficient to increase the pH of the antimicrobial solution to 3.5, and suffcent water to adjust the total weight % of the composition to 100%, the % weights based on the total weight of the antimicrobial solution. *Staphylococcus aureus* is incubated with the antimicrobial solution in accordance with the challenge protocol. The colony forming units of the *staphylococcus aureus* after 5 minutes is 268 microorganisms per milliliter. The colony forming units of the *staphylococcus aureus* after 10 minutes is less than 10 microorganisms per milliliter. *Pseudomonas aeruginosa* is then incubated with the antimicrobial solution in accordance 15 with the challenge protocol. The colony forming units of the *pseudomonas aeruginosa* after 5 minutes is less than 10 microorganisms per milliliter which is a much higher kill rate than the kill rate of the antimicrobial solution without an alkali base as a component.

FIG. 3 presents data of a non-toxic antimicrobial composition comprising acetic acid, rosemary oil, spearmint oil, sodium hydroxide, and suffcent water to adjust the total weight % of the composition to 100%, on microbial recovery and colony formation. The effect of the non-toxic antimicrobial solution on *staphylococcus aureus, pseudomonas aeruginosa, escherichia coli*, and *salmonella* is tested. The initial inoculum of the microorganism is 1,000,000 microorganisms per milliliter. The expression "less than 10" as shown in FIG. 3 denotes no microbial growth of the microorganism during incubation and therefore no microbial recovery. *Staphylococcus aureus* is a gram positive bacterium, and *pseudomonas aeruginosa* is a gram negative bacterium. *Salmonella* and *escherichia coli* are gram negative bacteria.

EXAMPLE 12

The antimicrobial solution comprises 4% acetic acid, 0.25% sodium hydroxide, 1% rosemary oil, 1% spearmint oil, and sufficient water to adjust the total weight % of the composition to 100%, the % weights based on the total weight of the antimicrobial solution. The antimicrobial solution is incubated with *Staphylococcus aureus* in accordance with the challenge protocol. The colony forming units of the *staphylococcus aureus* after 10 minutes is less than 10 microorganisms per milliliter. The antimicrobial solution is then incubated with *Pseudomonas aeruginosa* in accordance with the challenge protocol. The colony forming units of the *pseudomonas aeruginosa* after 10 minutes is less than 10 microorganisms 5 per milliliter.

The antimicrobial solution is then incubated with *Escherichia coli* in accordance with the challenge protocol. The colony forming units of *escherichia coli* after 10 minutes is less than 10 microorganisms per milliliter. The antimicrobial solution is then incubated with *Salmonella* in accordance with the challenge protocol. The colony forming units of the *salmonella* after 10 minutes is less than 10 microorganisms per milliliter.

The foregoing examples have been provided merely for the purpose of explanation and are in no way to be construed as limiting of the present method and system disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. An antimicrobial composition for cleaning, reducing bioburden, and substantially killing gram positive and negative bacteria on hard surfaces in about 5minutes, wherein said antimicrobial composition consists essentially of:
   a) about 0.01% to about 4.0% by weight of rosemary oil and spearmint oil,
   b) about 0.1% to about 4.0% by weight of acetic acid;
   c) sodium hydroxide or potassium hydroxide in an amount sufficient to produce an antimicrobial solution with a pH in a range of about 3.0 to about 4.0; and
   d) sufficient water to adjust total weight of the antimicrobial solution to 100%, wherein the % weights are based on the total weight of the antimicrobial solution.

2. The antimicrobial composition of claim 1, wherein said hard surfaces are selected from the group consisting of table surfaces, equipment surfaces, cutting boards, food processing equipment, food storage equipment, plastic containers, metal containers, and conveyor belts.

3. The antimicrobial composition of claim 1, wherein said bioburden is selected from the group consisting of microbial flora, molds, bacteria, yeast, viruses and organic matter.

* * * * *